United States Patent [19]
Tsai et al.

[11] Patent Number: 6,017,843
[45] Date of Patent: Jan. 25, 2000

[54] CATALYST COMPOSITION FOR PREPARING 5-FORMYL VALARIC ESTERS FROM PENTENOIC ESTERS

[75] Inventors: Jing-Cherng Tsai, Kaohsiung; Hsi-Hui Tai, Hsinchu Hsien; Tsai-Tien Su, Hsinchu; Bor-Ping Wang, Taoyuan, all of Taiwan

[73] Assignee: Industrial Technology Research Institute, Hsinchu, Taiwan

[21] Appl. No.: 09/100,845

[22] Filed: Jun. 19, 1998

[51] Int. Cl.$^7$ ...................................................... B01J 31/00
[52] U.S. Cl. ............................................. 502/166; 502/162
[58] Field of Search ..................................... 502/121, 158, 502/162, 166

[56] References Cited

U.S. PATENT DOCUMENTS 5,719,312  2/1998  Hansen et al. ........................... 560/177

*Primary Examiner*—Elizabeth D. Wood
*Attorney, Agent, or Firm*—W. Wayne Liauh

[57] ABSTRACT

The present invention discloses an improved catalyst composition for preparing 5-formylvalerate esters by hydroformylation of pentenoic esters monoxide with good activity, high selectivity in the presence of hydrogen and carbon.

4 Claims, No Drawings

CATALYST COMPOSITION FOR PREPARING 5-FORMYL VALARIC ESTERS FROM PENTENOIC ESTERS

FIELD OF THE INVENTION

The present invention relates to an improved catalyst composition for preparing 5-formylvalerate esters by hydroformylation of pentenoic esters in the presence of hydrogen and carbon monoxide. More specially, the present invention relates to an improved catalyst composition for preparing 5-formylvalerates with good activity, high selectivity and lower cost.

BACKGROUND OF THE INVENTION

The hydroformylation of 3-pentenoic esters for the preparation of linear 5-formyvalerate esters is a valuable process since 5-formylvalerate esters are important intermediates for the preparation of caprolactam. Processes for preparing 5-formyvalerate esters from hydroformylation of pentenoic esters are disclosed in EPO patent No. 295554 and U.S. Pat. No. 3,253,018. 4-pentenoic ester or acid is used as a reactant to undergo the carbonylation reaction, providing 5-formylvalerate or 5-formyl valeric acid as the major product in both the processes described above. These processes have very limited commercial applications, since 4-pentenoic ester is not readily available from simple reaction procedure. Processes for direct hydroformylation of 3-pentenoic esters are initially disclosed in EPO Patent No. 556,681 and U.S. Pat. No. 5,264,616. The inventions relate to processes for hydroformylation of 3-pentenoic esters with carbon monoxide and hydrogen in the presence of catalyst compositions comprising rhodium carbonyl complexes, and bidentate phosphite ligands of the formula (I) or formula (II):

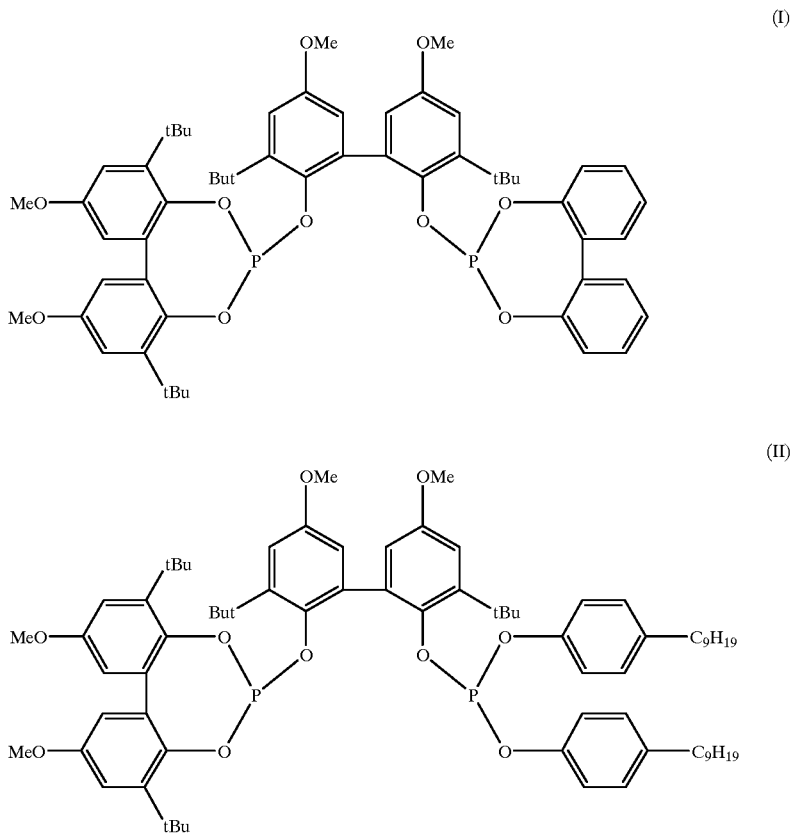

According to the invention disclosed in EPO Patent No. 556681, the catalyst system induces the hydroformylation of 3-pentenoic methyl ester to yield 5-formyl valerate ester with a reacting selectivity of 76.7 mol %. The disadvantages of these processes are that both phosphite ligand (I) and (II) are prepared from 2,2'-dihydroxy-3,3'-di-tertbutyl-5,5'-dimethoxybiphenyl which is a commercially unavailable starting material. Because of that both ligands derive from expensive raw materials, and thus the cost of preparing these ligands is high.

Other catalyst systems not using 2,2'-dihydroxy-3,3'-di-tertbutyl-5,5'-dimethoxybiphenyl for preparing phosphite ligands are disclosed in WO 95/18089. The catalyst compositions can be used for direct hydroformylation of 3-pentenoic esters in the presence of carbon monoxide and hydrogen to give the desired 5-formyl valeric esters. Again, the catalyst compositions comprise rhodium complexes and a chelating multidentate phosphite ligand of the formula (III):

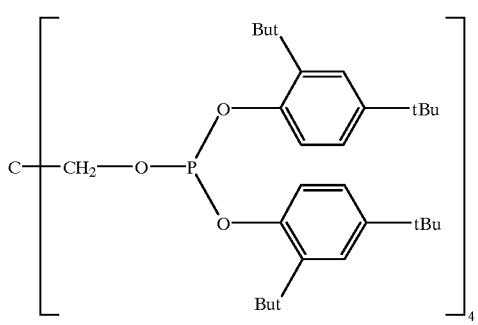

(III)

According to WO/18089, the highest selectivity for the hydroformylation of 3-pentenoic methyl ester to give methyl 5-formyl valerate can reach 80%. The disadvantages of the process are that the chelating phosphite ligand (III) is prepared from the insoluble pentaerythritol, thereby the preparation of the phosphite ligand (III) is difficult and the production cost is high.

All of the catalyst compositions described above for direct preparing 5-formyl valerate from pentenoic esters contain rhodium complexes and chelating phosphite ligands to provide activation ability. It should be noted that during the hydroformylation reaction, the phosphite ligands are easily oxidized and decomposed by hydroperoxide which is found in the presence of the starting pentenoic esters. As described by U.S. Pat. No. 5,527,950, extra amount of the phosphite ligand is required to constantly feed into the catalyst system for maintaining efficient reactivity. Therefore, from economic considerations, it is highly desirable to develop a catalyst composition which contains a low cost phosphite ligand while providing efficient activity toward hydroformylation of 3-pentenoic esters.

SUMMARY OF THE INVENTION

The primary object of the invention is to develop an improved catalyst composition for preparing 5-formyl valerate from 3-pentenoic esters with high selectivity. More specially, the primary object of the present invention is to develop an improved catalyst composition which allows the use of more economic ingredients for preparing the phosphite ligand, so as to substantially lower the cost of the catalyst composition, while providing high catalytic activity and selectivity in the process of hydroformylation of 3-pentenoic esters.

The catalyst composition disclosed in the present invention comprises the following components:

(a) 0.1 to 10 parts by mole of a rhodium complex represented by the following formula:

$$(Rh)_x(CO)_y(R)_z \qquad (IV)$$

wherein x is an integer of 1 to 6; y is an integer of 0 to 16; z is an integer of 0 to 2; R can be an acetate, an acetylacetonate or a halide; and (b) 0.1 to 200 parts by mole of a bidentate phosphite complex represented by the following formula:

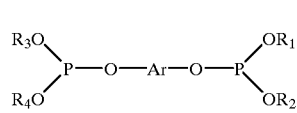

(V)

wherein $R_1$, $R_2$, $R_3$ and $R_4$ can be, independently, an alkyl group or an aryl group; Ar can be 2,2'-biphenol; 1,1'-bi-2-naphthol or 2,2'-ethylidenebis-(4,6-di-tert-butylphenol).

Preferably the catalyst composition disclosed in the present invention contains:

(a) 0.5 to 2 parts by mole of the rhodium complex; and (b) 0.5 to 40 parts by mole of the phosphite ligand complex.

The improved catalyst composition disclosed in the present invention can be used in combination with carbon monoxide and hydrogen for hydroformylation of 3-pentenoic esters to provide 5-formylvalerate with high activity and selectivity.

One of the advantages of the catalyst composition disclosed in the present invention is that the phosphite ligand is derived from commercially available inexpensive chemicals, therefore the cost of the catalyst composition is substantially reduced. Another advantage of the catalyst composition disclosed in the present invention is that the phosphite ligand can be easily prepared in a single reaction vessel (without purification of the intermediate product), wherein the phosphorus trichloride is reacted with the substituted phenol compounds in the presence of a hydrogen chloride acceptor (usually an tertiary amine compound) to produce the desired phosphite ligands with a high yield.

DETAILED DESCRIPTION OF THE PREFERRED EMBODIMENT

The present invention discloses an improved catalyst composition for hydroformylation of 3-pentenoic esters to give 5-formylvalerate and the process of utilizing this improved catalyst composition. The improved catalyst composition disclosed in the present invention allows the use of a economical ingredient for the preparation of the catalyst composition thus substantially lowering the manufacturing cost for preparing the phosphite ligand, while providing good activity and selectivity for hydroformylation of 3-pentenoic esters.

The catalyst composition disclosed in the present invention comprises the following components:

(a) 0.1 to 10 parts by mole of a rhodium complex represented by the following formula:

$$(Rh)_x(CO)_y(R)_z \qquad (IV)$$

wherein x is an integer of 1 to 6; y is an integer of 0 to 16; z is an integer of 0 to 2; R can be an acetate, an acetylacetonate or a halide.

(b) 0.1 to 200 parts by mole of a bidentate phosphite complex represented by the following formula:

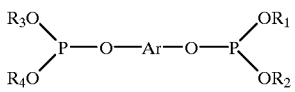
(V)

Wherein $R_1$, $R_2$, $R_3$ and $R_4$ can be, independently, an alkyl group or an aryl group; Ar can be 2,2'-biphenol; 1,1'-bi-2-naphthol or 2,2'-ethylidenebis-(4,6-di-tert-butylphenol).

Preferably the catalyst composition disclosed in the present invention contains:

(a) 0.5 to 2 parts by mole of the rhodium complex.

(b) 0.5 to 40 parts by mole of the phosphite ligand complex.

Examples of suitable rhodium compounds of formula (IV) are $Rh(CO)_2(acac)$ (acac=acetylacetonate); $Rh(OAc)_2$ (OAc=acetate); $Rh(OOtc)_2$ (OOtc=octanoate); $Rh_4(CO)_{12}$ and $Rh_6(CO)_{16}$.

Examples of suitable phosphite ligands of formula (V) are

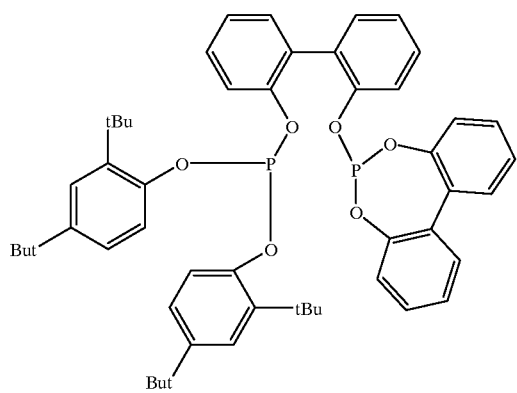
(VI)

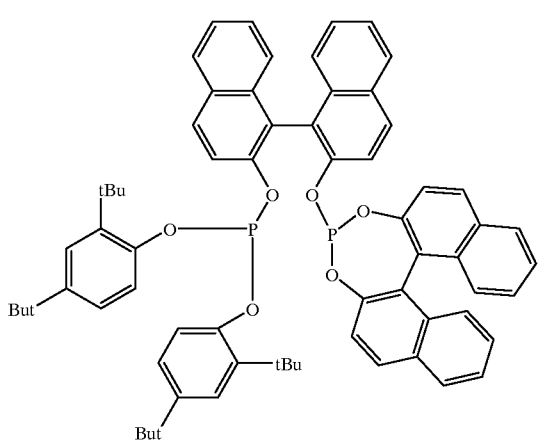
(VII)

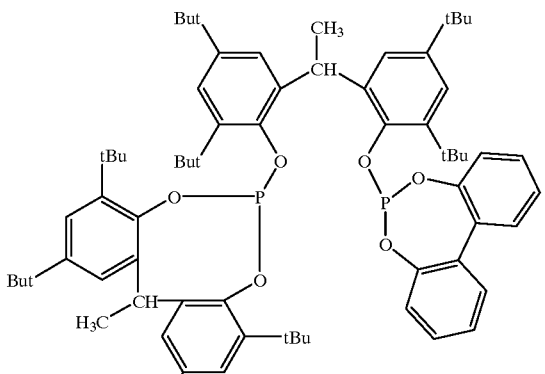
(VIII)

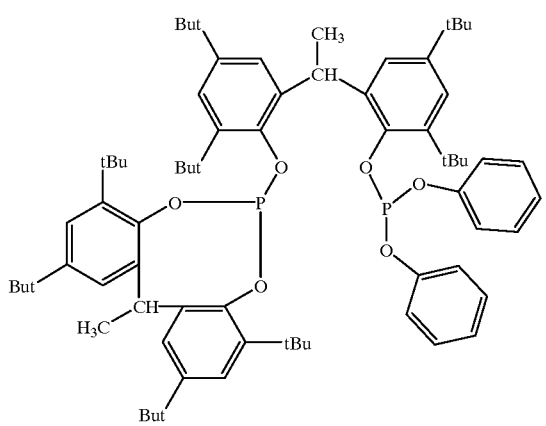
(IX)

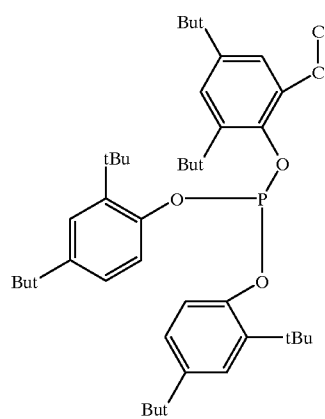
(X)

The hydroformylation process related to this present invention can be conducted in a high-boiling inert solvent, thereby removing the desired reaction product, 5-formyl valerate from the reaction mixture by distillation. The remaining catalyst components can be reused by feeding another portion of the 3-pentenoic ester and charging it with carbon monoxide and hydrogen for hydroformylation.

The present invention will now be described more specifically with reference to the following examples. It is to be noted that the following descriptions of examples, including the preferred embodiment of this invention, are presented herein for purposes of illustration and description, and are

Embodiments

EXAMPLE 1

10 g of 3-pentenoic methyl ester combined with 50 ml of diphenyl methane, 4.0 mg (0.0388 mmol) of rhodium dicarbonyl acetylacetonate and 0.24 g (0.23 mmol) of compound (VII) were provided and placed in a autoclave of 150 ml, which was equipped with an electrically powered stirrer. The autoclave was allowed to heat to 100° C. and was then charged with a 6-atm gas mixture containing 50% of carbon monoxide and 50% of hydrogen to start the hydroformylation reaction. The reaction was maintained at 100° C. under a 6-atm gas mixture of $CO/H_2$ during the reaction. After 8 hours, the analysis result of the reaction products indicated that the conversion rate of 3-pentenoic ester was 52%, the selectivity for the desired 5-formyl valerate was 69%, and the ratio of 5-formyl valerate to 3- and 4-formyl valerate was 76:24.

EXAMPLE 2

Example 1 was repeated, except that the phosphite ligand used was 0.24 g (0.23 mmol) of formula VIII. After 8 hours, the analysis result of the reaction products indicated that the conversion rate of 3-pentenoic ester was 82%, the selectivity for the desired 5-formyl valerate was 78%, and the ratio of 5-formyl valerate to 3- and 4-formyl valerates was 81:19.

EXAMPLE 3

Example 2 was repeated, except that the reaction was forwarded under a 10 atm mixture gas of $CO/H_2$. After 8 hours, the analysis result of the reaction indicated that the conversion rate of 3-pentenoic ester was 88%, the selectivity for the desired 5-formyl valerate was 74%, and the ratio of 5-formyl valerate to 3- and 4-formyl valerate was 76:20.

EXAMPLE 4

Example 2 was repeated, except that a pentenoic ester mixture containing 30% of 2-pentenoic methyl ester and 70% of 3-pentenoic ester was used for hydroformylaction instead of the pure 3-pentenoic methyl ester. After 8 hours, the analysis result of the reaction products indicated that the conversion rate of 3-pentenoic ester was 72%, the selectivity for the desired 5-formyl valerate was 76%, and the ratio of 5-formyl valerate to 3-and 4-formyl valerate was 79:18.

The preferred embodiments of the invention have been presented as above for the purposes of illustration and description. Obvious modifications or variations are possible in light of the above. The embodiments were chosen and described to provide the illustration of this invention and its practical application to thereby enable those skilled in the art to utilize the invention in various embodiments and with various modifications as are suited to the particular use contemplated. All such modifications and variation are within the scope of the present invention as determined by the appended claims when interpreted in accordance with the breadth to which they are fairly, legally, and equitably entitled.

What is claimed:

1. A catalyst composition for preparing 5-fomyl valerate from 3-pentenoic ester or a mixture of pentenoic esters, comprising:

(a) 0.1 to 10 parts by mole of a rhodium complex represented by the following formula:

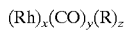

wherein x is an integer of 1 to 6, y is an integer of 0 to 16, z is an integer of 0 to 6; R can bean acetate, an acetylacetonate or a halide; and (b) 0.1 to 200 parts by mole of a bidentate phosphite ligand complex represented by the following formula:

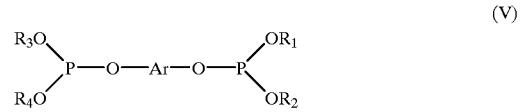

wherein $R_1$, $R_2$, $R_3$, and $R_4$ can be, independently, an alkyl group or an aryl group; Ar can be 2,2'-biphenol; 1,1'bi-2-ethylidenebis-(4,6-di-tert-butylphenol);

(c) further wherein said bidentate phosphite ligand is selected from the group consisting of:

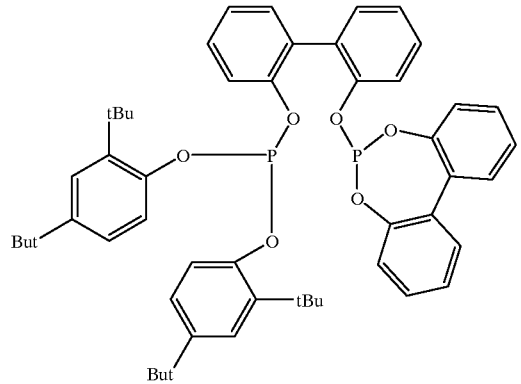

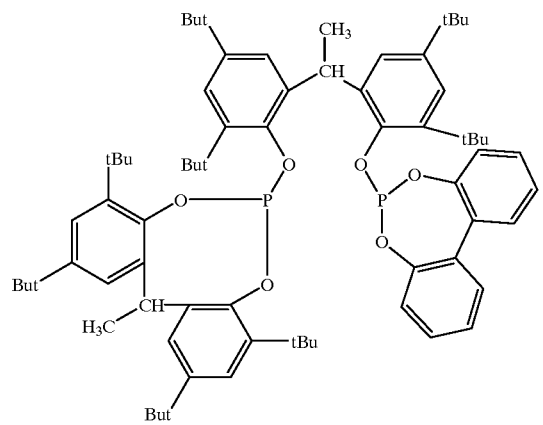

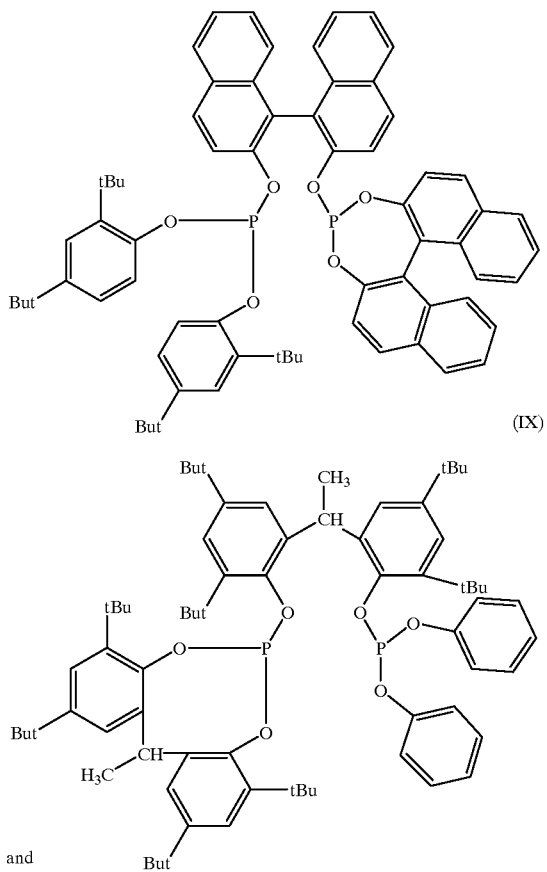

(VII)

(IX)

and

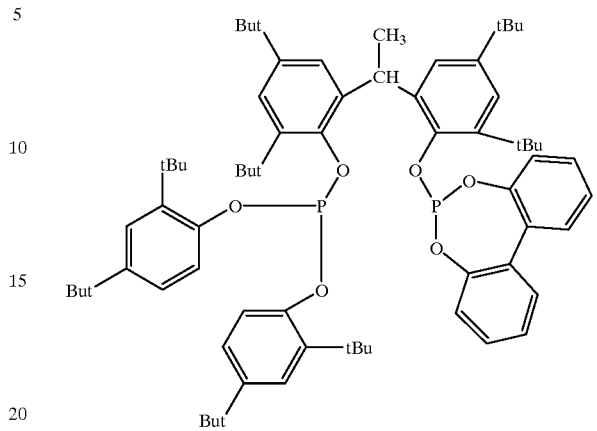

(X)

2. The catalyst composition as claimed in claim 1, wherein the rhodium compound is selected from the group consisting of $Rh(CO)_2(acac)$, $Rh(OAc)_2$, $[Rh(C_7H_{15}COO)_2]_2$, $Rh_4(CO)_{12}$ and $Rh_6(CO)_{16}$.

3. The catalyst composition as claimed in claim 2, wherein the content of the rhodium complex is about 0.1 to 2 parts by mole.

4. The catalyst composition as claimed in claim 1, wherein the amount of the bidentate phosphite ligand complex is about 0.5 to 40 parts by mole.

* * * * *